US005988386A

United States Patent [19]
Morrow

[11] Patent Number: 5,988,386
[45] Date of Patent: Nov. 23, 1999

[54] FEMININE HYGIENE STORAGE UNIT

[76] Inventor: Jacqueline M. Morrow, P.O. Box 5960, Fredericksburg, Va. 22406

[21] Appl. No.: 09/231,774

[22] Filed: Jan. 15, 1999

Related U.S. Application Data

[63] Continuation-in-part of application No. 09/044,983, Mar. 20, 1998.

[51] Int. Cl.[6] .......... A61F 13/26
[52] U.S. Cl. .......... 206/581; 206/440; 604/15
[58] Field of Search .......... 206/38, 216, 440, 206/581; 604/15, 358, 385.1, 904

[56] References Cited

U.S. PATENT DOCUMENTS

| | | | |
|---|---|---|---|
| D. 352,351 | 11/1994 | Garth . | |
| 1,768,203 | 6/1930 | Kole . | |
| 2,550,551 | 4/1951 | Gourdin . | |
| 2,750,033 | 6/1956 | Pickens . | |
| 3,035,578 | 5/1962 | Elmore . | |
| 3,058,469 | 10/1962 | Crockford . | |
| 3,135,262 | 6/1964 | Kobler et al. . | |
| 3,674,029 | 7/1972 | Bates et al. . | |
| 3,799,165 | 3/1974 | Wennerblom et al. . | |
| 3,818,912 | 6/1974 | Etz . | |
| 3,863,636 | 2/1975 | Johnson . | |
| 3,940,169 | 2/1976 | Kock . | |
| 3,973,567 | 8/1976 | Srinivasan et al. . | |
| 4,221,221 | 9/1980 | Ehrlich . | |
| 4,222,381 | 9/1980 | Widlund et al. . | |
| 4,271,835 | 6/1981 | Conn et al. | 604/15 |
| 4,312,348 | 1/1982 | Friese . | |
| 4,607,756 | 8/1986 | Courtman . | |
| 4,648,867 | 3/1987 | Conner et al. . | |
| 4,681,578 | 7/1987 | Anderson et al. . | |
| 4,777,969 | 10/1988 | Holloway . | |
| 4,848,572 | 7/1989 | Herrera . | |
| 4,881,278 | 11/1989 | Farah . | |
| 4,931,052 | 6/1990 | Feldman . | |
| 4,936,839 | 6/1990 | Molee et al. . | |
| 5,041,080 | 8/1991 | Shimatani et al. | 604/15 |
| 5,045,079 | 9/1991 | West . | |
| 5,180,059 | 1/1993 | Shimatani et al. . | |
| 5,242,057 | 9/1993 | Cook et al. . | |
| 5,336,208 | 8/1994 | Rosenbluth et al. . | |
| 5,342,331 | 8/1994 | Silber et al. . | |
| 5,346,486 | 9/1994 | Osborn, III et al. . | |
| 5,383,891 | 1/1995 | Walker . | |
| 5,409,116 | 4/1995 | Aronsen . | |
| 5,417,224 | 5/1995 | Petrus et al. . | |
| 5,429,627 | 7/1995 | Johnson et al. . | |
| 5,429,630 | 7/1995 | Beal et al. . | |
| 5,445,605 | 8/1995 | Pluss . | |
| 5,458,589 | 10/1995 | Comin-DuMong . | |
| 5,462,166 | 10/1995 | Minton et al. . | |
| 5,524,764 | 6/1996 | Kaufman et al. . | |
| 5,569,230 | 10/1996 | Fisher et al. . | |
| 5,579,916 | 12/1996 | Manko . | |
| 5,616,337 | 4/1997 | Kasianovitz et al. . | |
| 5,738,646 | 4/1998 | Fox et al. | 604/15 |
| 5,782,793 | 7/1998 | Nielson | 604/15 |
| 5,792,096 | 8/1998 | Rentmeester et al. | 604/15 |
| 5,800,377 | 9/1998 | Campion et al. | 604/15 |
| 5,891,081 | 4/1999 | McNelis et al. | 604/15 |

FOREIGN PATENT DOCUMENTS

| | | |
|---|---|---|
| 0 350 924 A2 | 1/1990 | European Pat. Off. . |
| 868299 | 5/1961 | United Kingdom . |
| 2 048 684 | 12/1980 | United Kingdom . |
| 2 094 637 | 9/1982 | United Kingdom . |

*Primary Examiner*—Jim Foster
*Attorney, Agent, or Firm*—Richard C. Litman

[57] ABSTRACT

A feminine hygiene storage unit includes a tampon section and a plunger section. Both sections are generally cylindrical and are coaxial to one another. The tampon section has a plunger end, an expulsion end, and a tampon compartment. The tampon compartment contains a tampon. The plunger section has a tampon end, a distal end, and at least one plunger compartment. The plunger section has a slightly smaller diameter than the tampon section. The plunger section is adapted to slide into the tampon section, expelling the tampon. The plunger compartment is adapted to contain a variety of menstrual products, such as a panty liner, a sanitary napkin, a moistened towelette, a tampon disposal bag, or a pharmaceutical composition for relief of menstrual symptoms.

20 Claims, 5 Drawing Sheets

10 12 14 16 18 21 22 23 26 27 28 29 29 30 31 32 34 44 48 52

FEMININE HYGIENE STORAGE UNIT

CROSS-REFERENCE TO RELATED APPLICATION

This application is a continuation-in-part of application Ser. No. 09/044,983, filed Mar. 20, 1998.

BACKGROUND OF THE INVENTION

1. Field of the Invention

The present invention relates to feminine hygiene products.

2. Description of the Related Art

Keeping clean and comfortable while experiencing menstrual discharge or menses is well known to be a difficult problem. The menstrual flow is variable and can be quite heavy at times. Menstruation can begin unexpectedly and may continue for several days. Once the menses have dried on the skin and in the pubic hair, they are difficult to remove with dry toilet paper. Menstrual discharge has a distinctive odor. Menstruation may be accompanied by or preceded by a variety of unpleasant symptoms, including cramps, water retention, mood changes, and nausea.

A variety of feminine hygiene products are in use for dealing with menstrual discharge. Of these, the most common are tampons, sanitary napkins, and panty liners. A typical tampon includes an absorbent section and a withdrawal string, both typically of cotton. The absorbent section is compressed into a cylindrical shape for insertion into the vagina.

Tampons are commonly packaged in an applicator to ease insertion. The most common applicator is the tube type, which has a pair of telescoping tubes with the withdrawal string extending through the hollow center of the inner tube. Generally the withdrawal string is long enough to dangle from the end of the inner tube before use. The applicator is generally packaged in a thin overwrap of paper or plastic. After insertion, the withdrawal string is left dangling outside the vagina so that the tampon is easily removed when saturated by pulling on the string.

A sanitary napkin ordinarily includes a top sheet on the body-facing surface, an absorbent layer, a liquid impervious back sheet, and adhesive fasteners on the garment-facing surface of the back sheet. A release strip or release paper protects the adhesive fasteners. Special highly absorbent materials may be used in the absorbent layer to lessen the bulk and increase the absorbency. The release paper is removed immediately prior to use, and the adhesive fasteners used to adhere the napkin to the crotch portion of an undergarment. A panty liner or panty shield is similar in construction to a sanitary napkin, but is generally smaller and thinner. An overwrap is occasionally provided for individual sanitary napkins; a common type is a tri-fold wrapper of thin paper or plastic.

Since tampons are used internally, they are inconspicuous and minimize odor. However, tampons cannot be left in place for more than a few hours, due to the risk of toxic shock syndrome. Some women alternate the use of tampons and sanitary napkins, to further reduce the risk of toxic shock. Since the tampon is invisible during use except for its withdrawal string, it can be difficult to determine when the tampon is approaching saturation. The first sign of saturation may be stained underclothing, which is a nuisance at best. Tampons occasionally fail to absorb well, such as when the menstrual discharge flows past the tampon, leading to embarrassing stains.

Many women use a panty liner or sanitary napkin with a tampon. This back-up prevents stains and makes it easy to see when a tampon is saturated and needs to be changed. A combination of a tampon and a sanitary napkin is also used to provide extra absorption by women who experience very heavy flow. The tampon and its back-up sanitary napkin or panty liner are frequently changed at the same time.

Since the menstrual flow often begins unexpectedly, it is desirable to have a tampon, sanitary napkin, or the like readily available at all times. Unfortunately, the typical packaging of feminine hygiene products is delicate and easily damaged by storage in a purse or the like. For example, when a tampon in its applicator is stored in a purse the overwrap typically breaks, and the tampon falls out of the applicator. This allows the tampon itself to mix with the contents of the purse, so that it becomes dirty and damaged. The fabric surface of a tampon picks up dirt easily and retains it. A tri-fold wrapper or similar packaging for sanitary napkins also provides very little protection in a purse. Unwrapped sanitary napkins also attract dirt. A dirty or damaged tampon or sanitary napkin is unpleasant to use, and may even be dangerous.

If a woman wishes to use a tampon in combination with a sanitary napkin or panty liner, both are carried separately. Since both are generally bulky and their shapes are quite different, this requires a significant amount of space in a purse. In any case, both are likely to become dirty or damaged, as described above.

Conventional feminine hygiene products are also difficult to dispose of in a sanitary manner. Handling a soiled tampon or sanitary napkin is unpleasant, so that the disposal means preferably does not involve direct contact with the hands. The typical thin overwrap is too small and delicate to be used for disposal. Some tampons are intended to be flushable, but flushin has an undesirable tendency to clog plumbing. Toilet paper may be used to wrap a used tampon or sanitary napkin. However, toilet paper soaks through easily and tends to disintegrate when wet. Toilet paper provides no protection against odor.

A number of harmful pathogens are spread by contact with the blood of an infected person. Spread of these diseases is possible through contact with menstrual blood. Many other harmful microorganisms find menstrual blood to be an ideal growth medium. Feminine hygiene products discarded unwrapped or wrapped in toilet paper therefore represent a public health risk.

U.S. Pat. No. 5,569,230 to Fisher et al. discloses an individually packaged sanitary napkin packaged with a cleansing wipe. The wipe pouch may be attached with a perforation so that it can be torn off and carried separately if desired. The wrapper of the sanitary napkin includes a flap or pouch for disposing of the used napkin and wipe. The cleansing wipe may also be packaged wrapped around a tampon and covered with a moisture impervious overwrap.

U.S. Pat. No. 4,607,756 to Courtman discloses a tubular container with two co-axial chambers for storing shampoo, conditioner, cosmetics, pharmaceuticals, condiments, and the like. One chamber may be smaller than the other.

U.S. Pat. No. 4,648,867 to Conner et al. discloses a tampon system which includes a tampon, a flexible sheath surrounding the tampon, a ring at one end, and a removable closure over the opening in the ring. The tampon is inserted by pushing the tampon through the sheath with a finger. The closure may be of paper, foil, or the like, and secured by a peelable adhesive. The closure may be resealable.

U.S. Pat. No. 4,848,572 to Herrera discloses a sanitary napkin having a shape conforming to the female genital area.

The sanitary napkin includes a moist towelette hermetically sealed in an elongate sheath. The sheath serves as the release strip for the adhesive fasteners.

U.S. Pat. No. 5,242,057 to Cook et al. discloses a personal care convenience kit which disclosed different personal hygiene components one at a time through a dispensing opening. The hygiene components include premoistened wipes, tissue paper, soap, and toilet seat covers.

U.S. Pat. No. 4,931,052 to Feldman discloses a disposable diaper with an integral moist towelette. The towelette is stored in a liquid impermeabel pocket. The pocket expands to form a disposal container for the soiled diaper and the spent towelette.

U.S. Pat. No. 4,881,278 to Farah disclosed a single-use unitary package having a compartment for a folded toilet seat cover and another compartment for a toilet seat disinfectant. U.S. Pat. No. 3,035,578 to Elmore discloses a cover for enclsoing sanitary napkins prior to use, which may be used for disposal. U.S. Pat. No. 3,058,469 to Crockford discloses a tampon holder having a telescopically-applied closure cap. U.S. Pat. No. 5,446,605 to Pluss discloses a tampon with a cylindrical sheath having a hole and two notches for the withdrawing thread. U.S. Pat. No. 3,818,912 to Etz discloses a tampon having a recess at one end with the draw string disposed within the recess.

U.S. Pat. No. 2,550,551 to Gourdin discloses a tubular convenience package for toilet seat cover and toilet paper, with perforations and a pull cord allowing separation into two halves. U.S. Pat. No. 5,462,166 to Minton et al. disclosed a flexible plastic wrapper for a sanitary napkin having relasable seals. U.S. Pat. No. 5,417,224 to Petrus et al. discloses a spherical tampon having a withdrawal thread in the form of a loop. U.S. Pat. No. 4,221,221 to Ehrlich discloses a diaper which includes sealed containers for a cleansing towel, baby powder, and the like. U.S. Pat. No. 5,180,059 to Shimatani et al. discloses a tampon package having three sheet parts folded to enclose the tampon. U.S. Pat. No. 5,579,916 to Manko discloses a clamshell-hinged kit for carrying feminine hygiene materials, including sanitary napkins, wipes, and disposal bags.

None of the above inventions and patents, taken either singularly or in combination, is seen to describe the instant invention as claimed. Thus a tampon with feminine hygiene storage unit solving the aforementioned problems is desired.

SUMMARY OF THE INVENTION

The present invention is a feminine hygiene storage unit which includes a tampon section and a plunger section. Both sections are generally cylindrical and are coaxial to one another. The tampon section has a plunger end, an expulsion end, and a tampon compartment. The tampon compartment contains a tampon. The plunger section has a tampon end, a distal end, and at least one plunger compartment. The plunger section has a slightly smaller diameter than the tampon section. The plunger section is adapted to slide into the tampon section, expelling the tampon. The plunger compartment is adapted to contain a variety of menstrual products, such as a panty liner, a sanitary napkin, a moistened towelette, a tampon disposal bag, or a pharmaceutical product for relief of menstrual symptoms.

Accordingly, it is a principal object of the invention to provide a feminine hygiene storage unit having a tampon section and a plunger section, the tampon section containing a tampon, the plunger section containing another menstrual product.

It is another object of the invention to provide a storage unit which can store hygiene products such as a tampon, panty liner, sanitary napkin, moistened towelette, disposal bag, cleansing mitt, or pharmaceutical composition.

It is a further object of the invention to provide a storage unit which protects feminine hygiene products from damage when stored in a purse.

Still another object of the invention is to provide a storage unit which stores menstrual products which are frequently used together compactly and securely.

Another object of the invention is to provide a storage unit for tampons and other menstrual products which includes a disposal bag to protect against the spread of disease.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is a feminine hygiene storage unit 10 which includes a tampon section 12 and a plunger section 14. Both sections are rigid, generally cylindrical, and coaxial to one another. The tampon section 12 is adapted to contain a tampon 22 and preferably is adapted to insertion into the vagina. The plunger section 14 is adapted to contain one or more menstrual products.

Both the tampon section 12 and the plunger section 14 are composed of paper, paperboard, cardboard, fiberboard, plastic, coated paper, or similar materials. These materials do not collect dirt, so that the exterior surface of the storage unit remains clean under typical storage conditions found in a purse. Multiple layers may be used if desired, such as a paper layer backed by a plastic layer. The material may include an anti-bacterial agent, if desired, to aid in the control of blood-borne pathogens after disposal.

Preferably the tampon section and the plunger section are each adapted to disposal after a single use. Inexpensive materials are therefore preferred for disposability. However, if desired the storage unit may be composed of a durable plastic or similar material which can be washed as necessary and reloaded with a tampon and another menstrual product.

Preferably the material of the storage unit 10 is water resistant or waterproof. This protects the contents from external dampness and damage due to moisture. Vice versa, if any of the menstrual products are themselves moist, the contents of the purse are protected from moisture. Water resistant material also allows the exterior surface of the storage unit to be rinsed prior to use, if desired. Rinsing may be done to remove excessive surface contamination or to lubricate the exterior surface of the tampon section for vaginal insertion.

The material is ideally sufficiently rigid for the storage unit 10 to be carried about, in a purse or otherwise, for a period of several months without being crushed or punctured. For any of the above materials, the minimum thickness of the tampon section or the plunger section is preferably no less than 1 millimeter, most preferably between 1 and 2 mm. If the thickness is too great, manufacturing costs are increased and the storage unit is uncomfortably heavy and bulky.

In a preferred embodiment both sections are composed of a coated paper which is adapted to biodegrade easily after use. This material is sufficiently water-resistant to protect the contents of the storage unit from external moisture. After use, the coated paper disintegrates under typical landfill conditions. This avoids the creation of environmental difficulties or litter problems. A suitable coating is available under the trade name Propecoat; other repulpable, polyurethane, replacement coatings are also acceptable.

Figure 1:
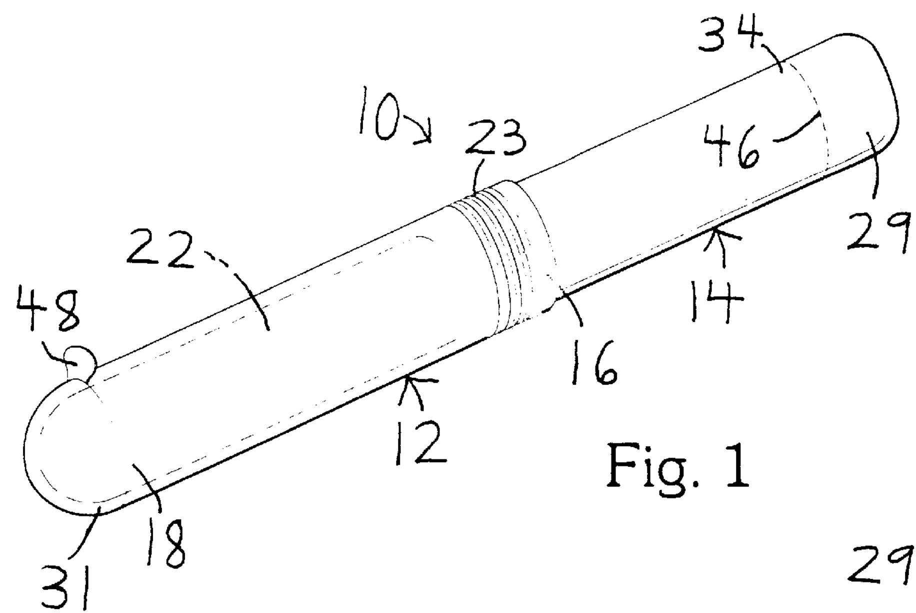
FIG. 1 is a perspective view of a storage unit according to the present invention.
Figure 2:
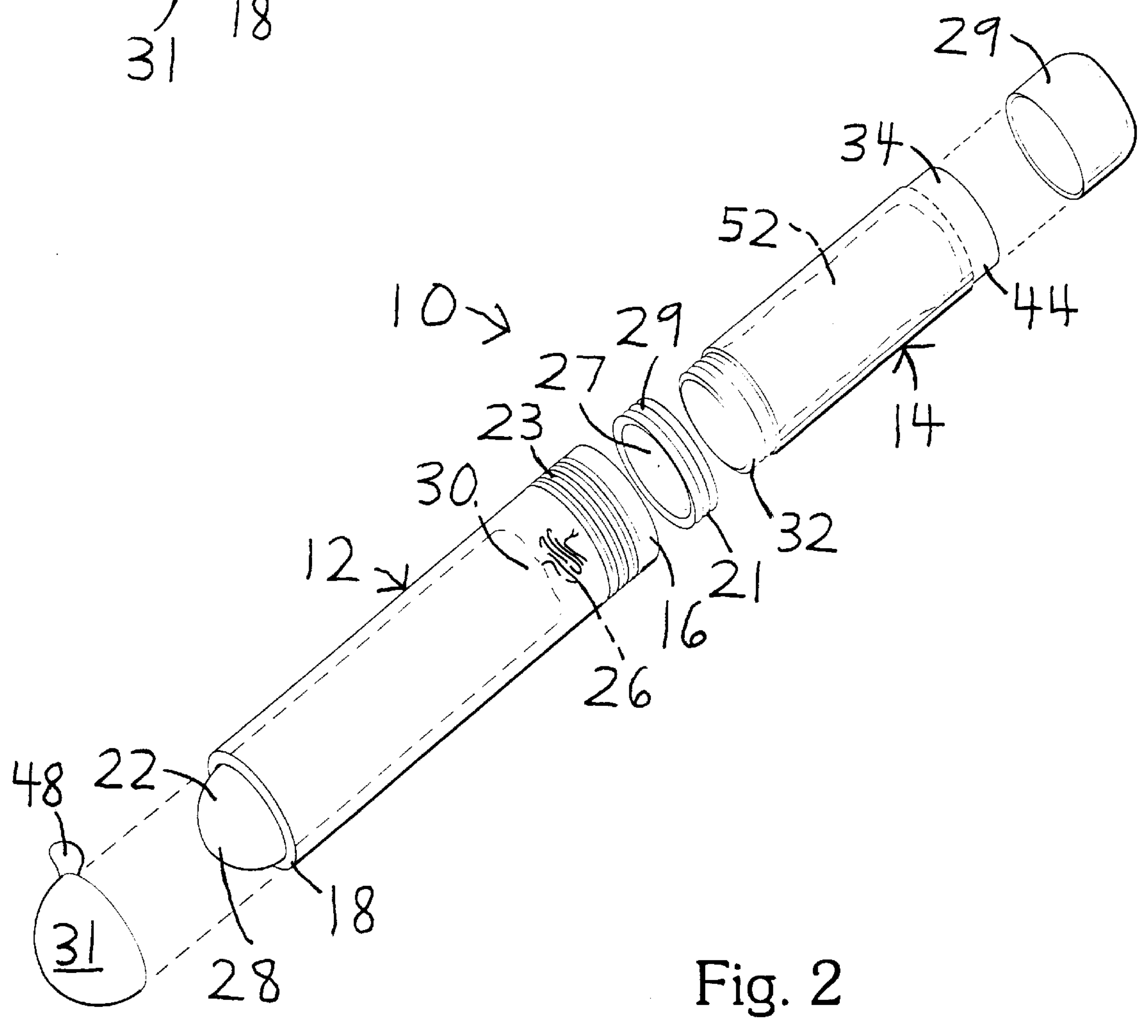
FIG. 2 is an exploded view of the storage unit of FIG. 1.

The tampon section 12 has an outer diameter and an outer surface. The tampon section 12 has a plunger end 16, an expulsion end 18, a tampon compartment 20, and a tampon 22. The outer diameter is preferably small enough for comfortable insertion into the vagina. Preferably the outer diameter is between about ½ and 1 inch. This makes insertion easier and more comfortable. The tampon section may include a series of circumferential finger ridges 23 near the plunger end 16, as shown in FIGS. 1 and 2. The finger ridges 23 make the tampon section easier to grasp during insertion. The grooves between the finger ridges 23 may extend through to form ridges and grooves on the interior surface of the tampon compartment.

The expulsion end 18 of the tampon section is preferably smooth with all edges being at least somewhat rounded. The expulsion end 18 may have a generally open-ended cylindrical configuration, as in FIGS. 2 and 3. This arrangement minimizes manufacturing costs.

Figure 11:
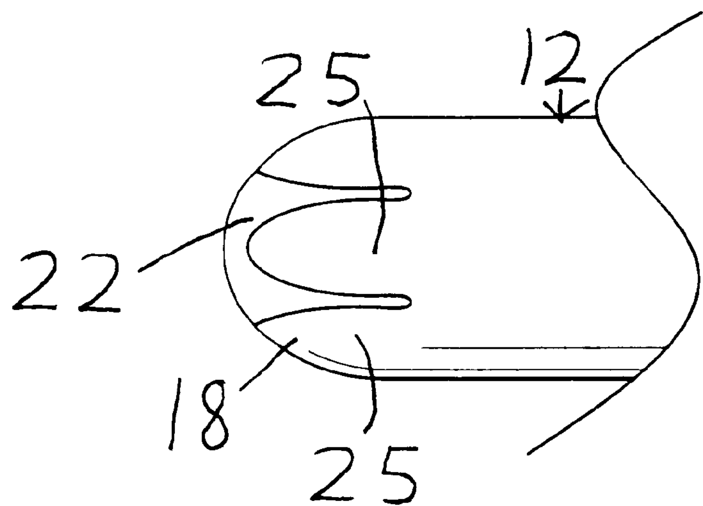
FIG. 11 is a detail, side view of an expulsion end of a tampon section having petals.

The expulsion end 18 may have a series of petals 25, ideally composed of flexible plastic. See FIG. 11. The petals 25 provide a very smooth surface for comfortable insertion in the vagina. Once inside the body, the petals 25 easily spread apart as the tampon 22 is expelled from the tampon section 12.

The tampon compartment 20 is adapted to contain the tampon 22. The tampon compartment preferably has a length and a diameter corresponding generally to the length and diameter respectively of the tampon.

Figure 3:
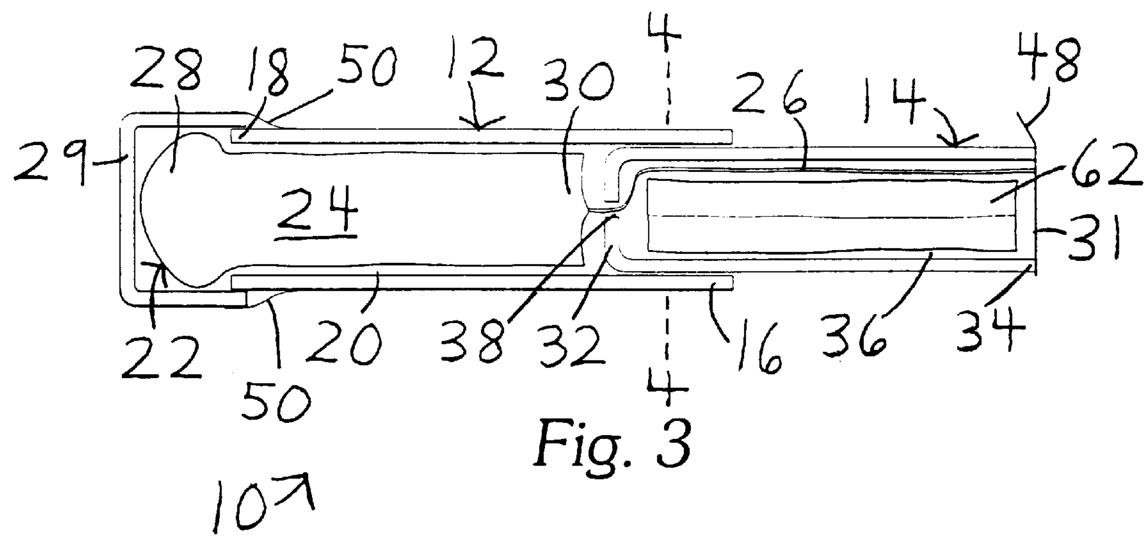
FIG. 3 is a fragmented, side view of a storage unit, showing part of the tampon section and plunger section removed.

The tampon 22 is located in the tampon compartment 20, as shown in FIGS. 1, 2, and 3. The tampon 22 preferably fits snugly in the tampon compartment 20. The tampon 22 has an absorbent portion 24 and a withdrawal string 26. The absorbent portion 24 has an expulsion end 28 and a plunger end 30. The tampon is typically compressed before use to a length of about 1 ½ to 2 inches and a diameter of about ⅜ to ¾ inches. The expulsion end 28 of the tampon is generally rounded for easier insertion, and may extend slightly past the expulsion end 18 of the tampon section 12. See FIGS. 1, 2, 3, and 11. The expulsion end 28 of the tampon 22 may have a slight bulge around its circumference, so that the edge of the expulsion end 18 of the tampon section is cushioned for insertion. The expulsion end 28 of the tampon may include a lubricated tip.

Figure 4:
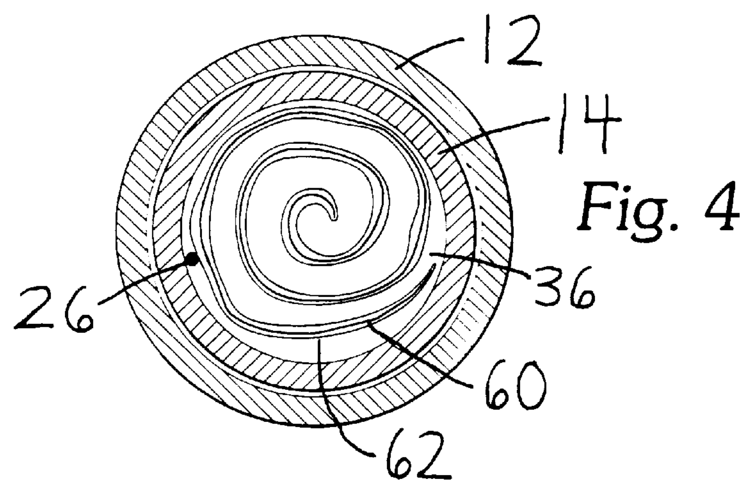
FIG. 4 is a cross-sectional view taken along line 4—4 of FIG. 3.
Figure 5:
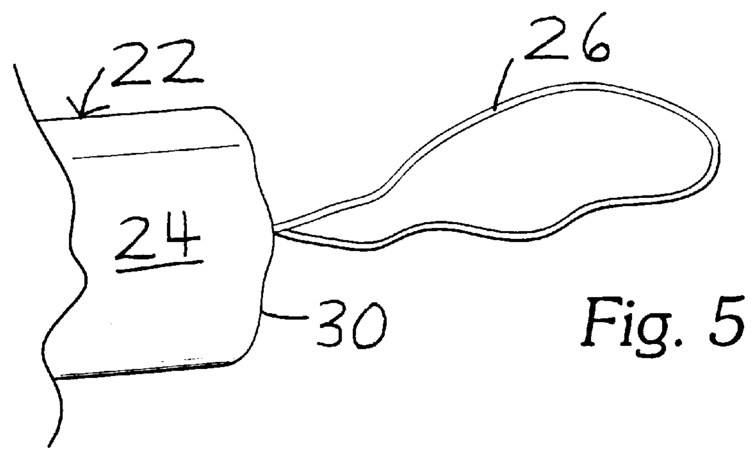
FIG. 5 is a detail view of a tampon and its withdrawal string.
Figure 6:
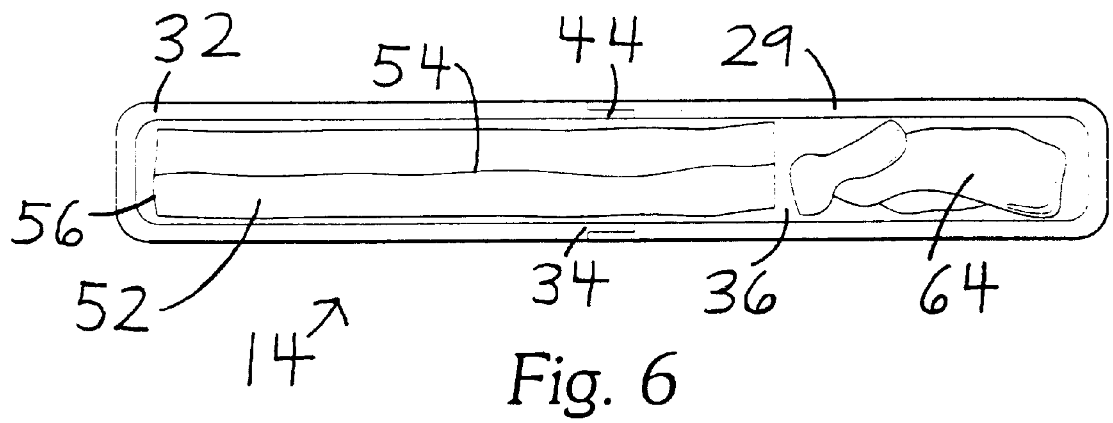
FIG. 6 is a fragmented, detail, side view of a plunger section containing a panty liner and a disposal bag.

The withdrawal string 26 is attached to the tampon 22 in any suitable manner. For example, the withdrawal string 26 may be stitched to the absorbent portion 24 or knotted around the absorbent portion. The withdrawal string may have a single strand, as shown in FIGS. 4 and 5, or a double strand, as shown in FIG. 6. Each strand may be composed of braided sub-strands, if desired. Preferably the withdrawal string 26 is a loop, as shown in FIG. 5. A loop allows for easy removal of the tampon 22 by simply hooking a finger through the loop and pulling. An adequate length for the loop is about two inches from the plunger end 30 of the tampon.

Ideally the tampon 22 is adapted to insertion into the vagina using the storage unit 10 as an applicator. However, the tampon 22 may be ejected from the storage unit 10 and then inserted by hand into the vagina. This arrangement requires the use of hand insertion, which is somewhat less comfortable for most women. However, for a non-disposable storage unit the necessity of washing the storage unit after use is avoided. Even for a disposable storage unit, it may be desirable to avoid insertion of the tampon section into the vagina if the exterior surface of the storage unit has been excessively contaminated.

Figure 7:
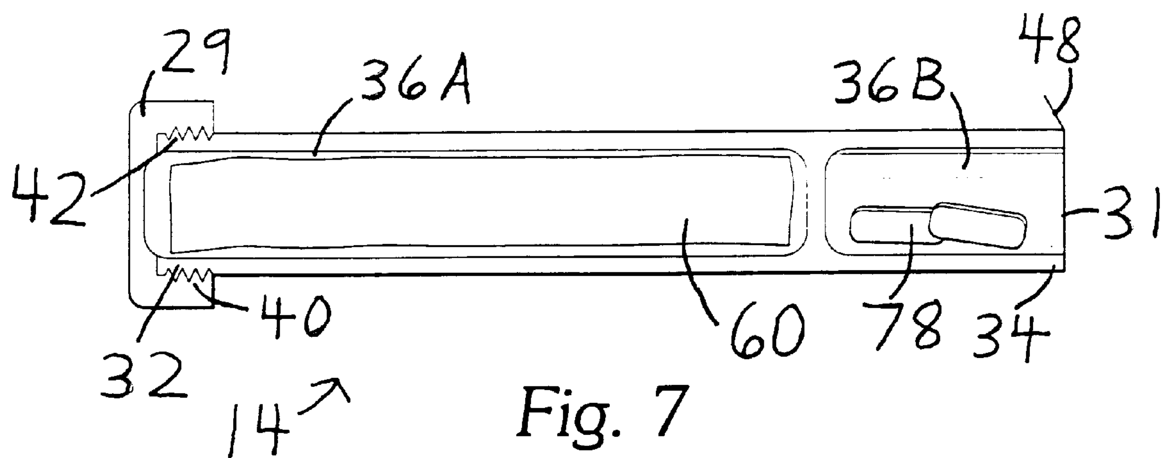
FIG. 7 is a fragmented, detail, side view of a plunger section having two plunger compartments containing a moistened towelette and a pharmaceutical composition respectively.

The plunger section 14 is separate from the tampon section 14 but is attached to the tampon section prior to use. The plunger section 14 is coaxial with the tampon section 12. The plunger section 14 has an outer diameter, a tampon end 32, a distal end 34, and at least one plunger compartment 36. The plunger section 14 may include a single plunger compartment 36, as shown in FIGS. 3 and 6. Alternatively, the plunger section may have first and second plunger compartments 36A and 36B, as shown in FIG. 7. Preferably the plunger compartments 36A and 36B are coaxial to one another. Preferably the plunger section has no more than two plunger compartments.

The outer diameter of the plunger section 14 is smaller than the diameter of the tampon compartment 20. The tampon end 32 of the plunger section is located before use within the plunger end 16 of the tampon section. The tampon end 32 of the plunger section is therefore proximate to the plunger end 30 of the tampon. Preferably the tampon end 32 of the plunger section includes a detent means to hold the plunger section in place within the tampon section prior to use. For example, the tampon end 32 may have one or more detent ridges 21 corresponding to grooves on the interior of the tampon compartment near the plunger end 16. See FIG. 2. The detent means also prevents the tampon 22 from falling out of the tampon compartment 20 through the plunger end of the tampon section.

The plunger section 14 is adapted to slide into the tampon compartment 20 so that the tampon 22 is ejected through the expulsion end 18 of the tampon section 12. Preferably the plunger section telescopes completely or nearly completely into the tampon compartment. If desired, the storage unit 10 may therefore be used for insertion of the tampon into the vagina, in the same way as a conventional tube type tampon applicator.

The storage unit 10 is adapted to contain at least one other menstrual product within the plunger compartment 36. Preferably the storage unit contains no more than three menstrual products in addition to the tampon, most preferably two or less. A larger number tends to make the storage unit undesirably bulky. Ideally the menstrual product is prepackaged in the plunger compartment 36. Alternatively, the storage unit 10 may be provided with an empty plunger compartment for an individual woman to fill with the menstrual product she prefers.

Preferably the expulsion end 18 of the tampon section and at least one of ends of the plunger section each include a closing means for releasably closing the tampon compartment and plunger compartment respectively. The closing means on the expulsion end 18 prevents the tampon 22 from falling out of the storage unit during storage in a purse. Preferably both the tampon end 32 and the distal end 34 of the plunger section are closed. The tampon end 32 may have an integral closure, as in FIG. 6. In a preferred embodiment the distal end 34 has a releasable closing means and the tampon end 32 has an integral closure. This configuration allows access to the plunger compartment without removing the plunger section from the tampon section. If the plunger section has first and second plunger compartments 36A and 36B, each plunger compartment has a releasable closing means so that the contents of both are accessible. See FIG. 7.

Suitable releasable closing means include a cap 29, a seal 31, a plug, or the like. Several different configurations are possible. The tampon compartment or the plunger compartment may extend into the closing means, as in FIGS. 1, 2, 3, and 6. The cap 29 may have an outer diameter similar to that of the section to which it is attached, as in FIGS. 1, 2, and 6. This configuration provides a smooth exterior surface with less opportunity for catching on objects. The corresponding section may include a reduced diameter cap seat 44 for the cap 29 to mate with.

The cap 29 may have a larger diameter than the corresponding section, as in FIGS. 3 and 7. A reduced diameter cap seat is not required. This allows the corresponding section to have a uniform diameter, reducing manufacturing costs.

The cap 29 may have female threads 40 and attach to male threads 42 on the tampon end 32, distal end 34, or expulsion end 18. See FIGS. 2 and 7. A threaded connection allows the cap to be repeatedly removed and replaced, but is more expensive to manufacture than other types of closures.

A less expensive closure is a simple frictional closure. Friction between the cap 29 and its cap seat 44 may be sufficient to retain the cap 29, without the aid of threads. A circumferential ridge and groove arrangement may also be used so that the cap snaps into place.

A series of frangible perforations 46 may attach the cap 29 to one of the ends, as shown in FIGS. 1 and 2 for the distal end 34. The cap may be removed initially by twisting the cap to break the perforations. If desired, the cap 29 may be replaced after use, with a frictional or threaded closure retaining the cap in place. See distal end 34 of FIG. 2. A string, pull-off tape or pull tab may be present to aid to breaking the perforations. If the storage unit 10 is composed of plastic, a series of frangible bridges may be more suitable than perforations. Bridges or perforations provide clear indication of any tampering, which is desirable for feminine hygiene products. However, bridges or perforations attaching a cap 29 to the expulsion end 18 may leave rough edges after opening, interfering with comfortable vaginal insertion of the tampon section 12.

Another closure means is shown in FIG. 3. The cap 29 is attached to the expulsion end 18 with frangible tabs 50 of paper tape or a similar material. Alternatively, a frangible strip of tape may extend around the entire circumference of the cap.

Another possible closure means is a plastic covering shrink-wrapped around the end to be closed. The plastic covering may be used alone or to secure a separate cap. The plastic covering may have perforations so that it tears away readily prior to use. The entire storage unit 10 may be shrink-wrapped in plastic, if desired. A shrink-wrapped plastic covering provides excellent moisture resistance and tamper indication, but generally cannot be resealed.

A seal 31 may be used as the releasable closing means. The seal 31 may be composed of aluminum foil or other foil, plastic, coated paper, etc. The seal may have several layers. For instance, a foil layer may be backed by a plastic layer to provide strength, moldability, and moisture resistance. Preferably the seal 31 includes a tab 48 to make the seal easier to remove. The tab 48 preferably is integral with the main portion of the seal 31. The seal 31 may be adapted to tear off or peel off to open the compartment. The seal 31 may be attached with a reusable adhesive so that the compartment may be resealed after opening. A foil seal 31 may be adapted to reseal the compartment by molding the seal back into place after opening. The seal 31 may have a diameter larger than the diameter of the sealed end.

The seal may be flat, as in FIGS. 3 and 7, or rounded, as in FIGS. 1 and 2. A flat seal is inexpensive to manufacture. A rounded seal permits the expulsion end 28 of the tampon to extend beyond the expulsion end 18 of the tampon section. A rounded seal may also be used to seal petals 25 prior to use.

The withdrawal string 26 may have several different locations in the storage unit 10. For example, the withdrawal string 26 may be compressed between the plunger end 30 of the tampon and the tampon end 32 of the plunger section. See FIG. 2.

If the tampon end 32 of the plunger section is closed, it may include a recess 27 on its outer surface. The withdrawal string 26 is at least partially contained within the recess 27. If the tampon end 32 includes a cap 29 or a seal 31, the recess 27 may be located on the outer surface of the cap or the seal. The recess prevents the withdrawal string from slipping between the tampon section and the plunger section and possibly jamming the ejection of the tampon. This location has the disadvantage, however, that the withdrawal string may be inserted into the vagina with the tampon and may be difficult to locate later for tampon removal.

Another possible location for the withdrawal string 26 is shown in FIGS. 3 and 4. The tampon end 32 of the plunger section may have an aperture 38, or the tampon end 32 may be completely open. In this case, the withdrawal string 26 may extend between the menstrual product and the inner surface of the plunger compartment 36, as shown in FIGS. 3 and 4. This location prevents the withdrawal string from being inserted into the vagina, but requires that the tampon end of the plunger section be at least partially open.

Figure 12:
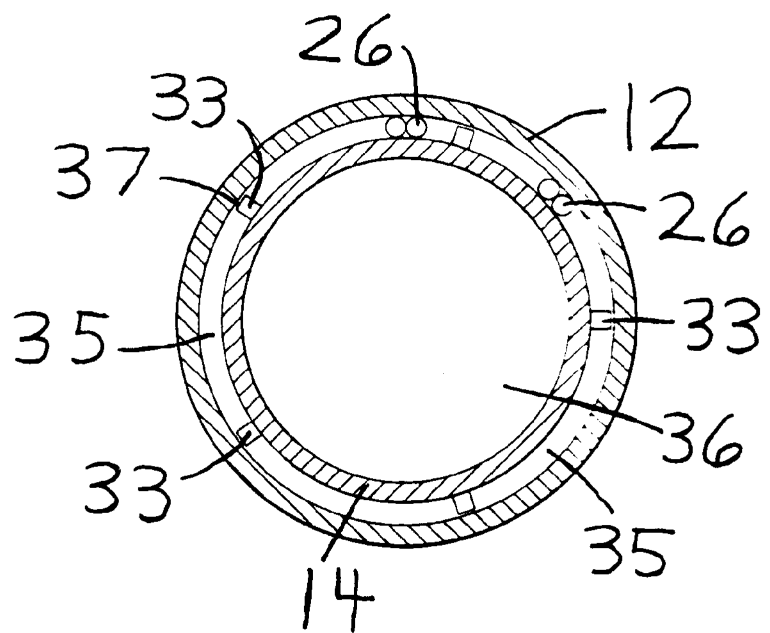
FIG. 12 is a cross-sectional view of a storage unit, showing a plunger section having exterior ridges and grooves.

Another possible configuration for the withdrawal string 26 is shown in FIG. 12. FIG. 12 shows a cross-sectional view of a storage unit 10 in the region of the plunger end 16 of the tampon section. The contents of the plunger compartment 36 have been omitted for clarity. The outer surface of the plunger section 14 has a plurality of exterior ridges 33 and a plurality of grooves 35. Five exterior ridges 33 are sufficient. Each exterior ridge 33 extends parallel to the longitudinal axis of the plunger section 14. The peak 37 of each exterior ridge 33 contacts the inner surface of the tampon compartment 20 as the plunger section 14 telescopes into the tampon compartment. The grooves 35 are located between the exterior ridges 33. The grooves 35 are adapted to contain the withdrawal string 26, as shown in FIG. 12. Since the withdrawal string 26 lies mostly or completely in the grooves, it does not jam between the tampon compartment and the plunger section.

If the withdrawal string 26 is a loop it may cross one or more exterior ridges 33. FIG. 12 shows a two-strand withdrawal string formed into a loop. Since the crossing point has a small area relative to the entire area of the exterior ridges, the smooth sliding of the plunger section is not significantly affected.

In a preferred embodiment the plunger section 14 is adapted to separate from the tampon section 12 after ejection of the tampon 22. See FIGS. 6 and 7. This allows retention of the menstrual product in the plunger section for use at a later time, if desired.

A wide variety of menstrual products may be contained in the plunger compartment or compartments. The menstrual product may be a hygienic product designed to absorb the menstrual flow or to maintain cleanliness during the menstrual period. Examples include a panty liner, sanitary napkin, moistened towelette, disposal bag, mitt, tissue, and toilet seat cover. The menstrual product may be a pharmaceutical composition adapted to relieving menstrual symptoms. The menstrual product in the plunger compartment may even be an additional tampon, if desired. The additional tampon might be adapted for hand insertion, or might be placed in the tampon compartment after the first tampon is used.

Figure 8:
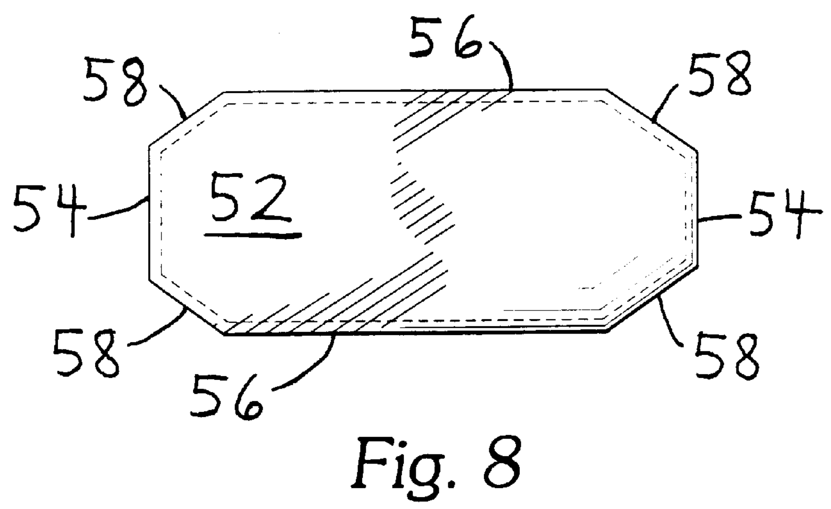
FIG. 8 is a detail, top plan view of a panty liner.

A preferred menstrual product is a panty liner 52, as shown in FIGS. 2, 6, and 8. The panty liner 52 has two ends 54 and two side edges 56. The panty liner 52 is preferably rolled lengthwise to fit into the plunger compartment 36, with one end 54 near the center of the roll and the other end 54 adjacent to the inner surface of the plunger compartment. Preferably the panty liner is rolled with the release paper on the outside, to facilitate removal from the plunger compartment. The side edge 56 nearest the closing means may have a tab to facilitate pulling the panty liner 52 out of the plunger compartment, similar to tab 48.

A panty liner 52 having a length of about 4 ½ inches, a width of about 2 inches, and a thickness of about 1⁄16 inch fits readily into a plunger compartment having a diameter of about ½ inch and a length of about 2 ¾ inches. A larger diameter plunger compartment will accommodate a larger panty liner or a sanitary napkin. Due to the limited space available in the plunger compartment, highly absorbent materials such as absorbent gels are preferably included to reduce the bulk of a panty liner or sanitary napkin.

In a preferred embodiment, the panty liner 52 has a generally rectangular shape modified by removing the corners. The panty liner 52 therefore has four corner edges 58. Each corner edge 58 connects one of the ends 54 to one of the side edges 56. Each corner edge 58 is at an angle to both the ends 54 and the side edges 56. See FIG. 8. The panty liner 52 is preferably somewhat smaller in area than the typical panty liner. The modified rectangular shape allows a small panty liner to roll compactly while providing adequate stain protection in use. The modified rectangular shape is also suitable for a sanitary napkin.

Packaging a tampon together with a panty liner or sanitary napkin in the storage unit has several benefits. Separate packages do not have to be carried, and both are available when needed. The storage unit is compact, durable, and easy to handle. The long cylindrical shape fits easily into a purse. The tampon is protected from dirt and damage. When a panty liner or sanitary napkin is used for back-up to a tampon or to provide additional absorbency, it is convenient to have both available in one package. The storage unit makes it easy to change both at the same time.

The storage unit also makes it easy to alternate the use of tampons and sanitary napkins to avoid toxic shock syndrome. Since the tampon compartment and the plunger compartment have separately releasable closures, either the tampon or the sanitary napkin can be used first. If the tampon is used first, the tampon section can be discarded and the sanitary napkin in the plunger compartment retained for later use.

The menstrual product may be a moistened towelette 60, as shown in FIGS. 3, 4, and 7. The towelette 60 is preferably composed of nonwoven material moistened with a cleansing solution. Suitable towelettes are well known in the art. The cleansing solution may include an antibacterial agent or a perfume. The towelette may be flushable. A typical towelette is rectangular and has a size of about 6 inches by 8 inches. The towelette 60 may be rolled and/or folded to fit into the plunger compartment 36. The edge of the towelette may have a tab extending from it adjacent to the closing means, to facilitate pulling the towelette out of the plunger compartment.

Since the towelette 60 is moist, it must be protected from contact with the tampon 22 and other items subject to moisture damage. The towelette 60 may be enclosed in a waterproof plunger compartment 36, as shown in FIG. 7. If the material of the plunger section 14 is not water resistant, the plunger compartment 36 may have a waterproof lining, such as a plastic or wax coating. Alternatively, the towelette 60 may be enclosed in a waterproof packet, such as a foil packet 62. Suitable towelettes in foil packets are commercially available. FIG. 3 shows a moistened towelette 60 in a foil packet 62, rolled to fit inside a plunger compartment 36. FIG. 4 shows a cross-sectional view taken along line 4—4 of FIG. 3, showing the rolled packet 62 and the towelette 60 inside the packet. The withdrawal string 26 is shown extending into the plunger compartment 36 and located between the foil packet 62 and the inner surface of the plunger compartment. Due to the protection provided by the foil packet, a waterproof plunger compartment is not necessary.

Providing a moistened towelette together with a tampon has several advantages. It eliminates the need to carry a separate package of towelettes. The combination is compact and easy to use. The towelette is readily available for cleansing the genital area and/or the hands when the tampon is changed. The towelette is more durable and cleans more thoroughly than toilet paper. Dried-on menses are easily cleaned. The hands can be cleaned even when water is not available, as on a hiking trip.

The menstrual product contained in the plunger compartment 36 may be a disposal bag 64. See FIGS. 6 and 9. The disposal bag 64 is adapted to contain one or more menstrual products for disposal. The disposal bag 64 is waterproof or water resistant. The disposal bag 64 may be composed of a thin, flexible plastic. The disposal bag has a closed end 66 and a releasably closed end 68. The releasably closed end 68 may have a variety of sealing means, such as a drawstring 70, an adhesive strip, or an incorporated twist-tie. A flexible plastic tongue-and-groove fastener (commercially available under the trademark ZIPLOC) may be used as the sealing means. The sealing means is preferably airtight and waterproof. This prevents the escape of unpleasant odors and keeps the menstrual discharge contained. The public health risks of exposure to blood are avoided.

Figure 10:
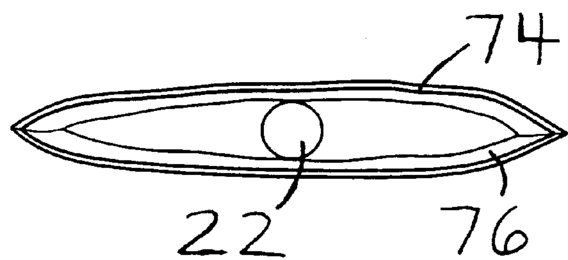
FIG. 10 is a cross-sectional view taken along line 10—10 of FIG. 9, showing a two-layer mitt turned inside out with a discarded tampon sealed within for disposal.

The disposal bag may be used in several situations to improve cleanliness. When changing a saturated tampon, the closing means may be removed first from the distal end of the plunger section. The disposal bag is then removed from the plunger compartment. The closing means may be replaced if desired. The saturated tampon is then removed and placed in the disposal bag, as shown in FIG. 10. The closing means is removed from the expulsion end of the tampon section to free the new tampon. The tampon section is then inserted in the vagina and the plunger section pushed in to expel the tampon from the storage unit into the vagina. The tampon section is removed from the vagina, leaving the tampon in place.

If the plunger compartment contains an additional hygienic product, it may then be removed and used. For example, a towelette may be used to clean the genital area. If the plunger compartment contains any additional hygienic products, the plunger section may be separated from the tampon section and retained for use later. Otherwise, the storage unit may be discarded in the disposal bag with the saturated tampon.

The disposal bag 64 may be a mitt. The mitt is adapted to cover a woman's hand during cleansing. The mitt may have a first layer 74 and a second layer 76, as shown in FIG. 10. The first layer 74 is preferably composed of thin, flexible plastic. The second layer 76 may be composed of moist towelette material. Before use, the two-layer mitt is packaged in the plunger compartment with the plastic first layer 74 on the inside and the towelette second layer 76 on the outside. The woman slips the mitt over her hand, so that the first layer 74 is adjacent to her hand. She then uses the mitt to remove a tampon or whatever is necessary. The towelette second layer 76 is used to cleanse herself. When finished, she pulls off the mitt, turning it inside out. This leaves the plastic first layer on the outside and the towelette second layer on the inside, as shown in FIG. 10. The mitt can then be sealed and discarded as a neat waterproof package. Any hygienic products being discarded at the same time can be placed inside the mitt, as in FIG. 10. There is no need for the woman's hand to actually touch a soiled tampon or panty liner.

Figure 9:
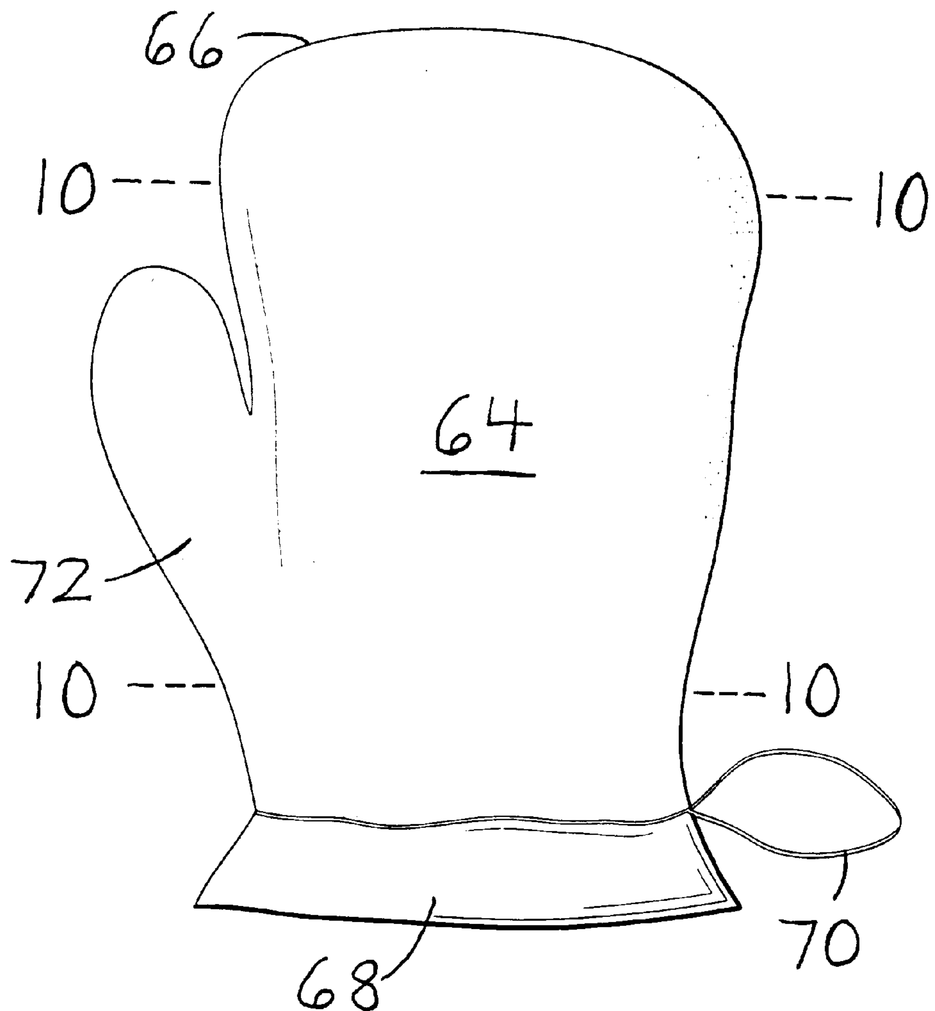
FIG. 9 is a detail, perspective view of a mitt.

The mitt may have a simple bag shape, with the bag being large enough to fit over a woman's hand. Alternatively, the mitt may have a separate thumb portion 72, as shown in FIG. 9. This provides more freedom of movement but increases the expense of manufacture. The mitt may have the shape of a glove with separate finger portions for each finger.

The menstrual product contained in the plunger compartment 36 may be a pharmaceutical composition adapted to relieving menstrual symptoms. Pharmaceuticals for the relief of pain, bloating, nausea, irritability, and the like associated with menstruation are well known in the art. FIG. 7 shows two tablets 78 sealed in plunger compartment 36B. Since tablets and capsules are generally subject to damage from moisture, they must be isolated from moistened towelettes. This may be done by placing tablets 78 and towelette 60 in separate waterproof compartments, as in FIG. 7. Alternatively, the tablets 78 may be sealed in one or more foil packets or other protective packaging before placement in the plunger compartment 36. Suitable protective packaging for individual doses of pharmaceutical compositions is well known.

Storage of a pharmaceutical composition for relief of menstrual symptoms together with a tampon and possibly other hygienic products has several benefits. The dosing schedule for pain relief compositions is often similar to the schedule for changing tampons. When a menstrual period begins unexpectedly and unpleasant symptoms are experienced, it is convenient to have available both a tampon to deal with the discharge and a pharmaceutical to deal with the symptoms. A package containing an individual dose of a pharmaceutical tends to fall to the bottom of a purse and is hard to locate when needed. Storing the pharmaceutical in the storage unit with a tampon assures that both can be found quickly. If premenstrual symptoms are experienced, the pharmaceutical can be removed for use and the tampon retained in the storage unit until needed.

It is to be understood that the present invention is not limited to the embodiments described above, but encompasses any and all embodiments within the scope of the following claims.

I claim:

1. A feminine hygiene storage unit, comprising:

(a) a tampon section, the tampon section being rigid and generally cylindrical, the tampon section having an outer diameter, a plunger end, an expulsion end, a tampon compartment, and a tampon, the tampon being located in the tampon compartment and having a withdrawal string, the tampon compartment being adapted to contain the tampon;

(b) a plunger section separate from and attached to the tampon section, the plunger section being coaxial with the tampon section, the plunger section being rigid and generally cylindrical, the plunger section having an outer diameter, a tampon end, a distal end, and at least one plunger compartment, the outer diameter of the plunger section being smaller than the diameter of the tampon compartment, the tampon end of the plunger section being located within the plunger end of the tampon section proximate to the tampon, the plunger section being adapted to slide into the tampon compartment so that the tampon is ejected through the expulsion end of the tampon section; and (c) at least one other menstrual product contained within the plunger compartment.

2. The storage unit of claim 1, wherein the tampon section and the plunger section are each adapted to disposal after a single use.

3. The storage unit of claim 1, wherein the tampon section and the plunger section are composed of a material selected from the group consisting of coated paper, paperboard, cardboard, and plastic.

4. The storage unit according to claim 1, wherein the tampon section is adapted to comfortable insertion into a vagina.

5. The storage unit according to claim 1, wherein the tampon end of the plunger section is closed and includes a recess, and the withdrawal string is at least partially contained within the recess.

6. The storage unit according to claim 1, wherein the plunger section has a longitudinal axis and an outer surface, the outer surface of the plunger section has a plurality of exterior ridges and a plurality of grooves, each exterior ridge extends parallel to the longitudinal axis, the grooves are located between the exterior ridges, and the grooves are adapted to contain the withdrawal string.

7. The storage unit according to claim 1, wherein the expulsion end of the tampon section and at least one end of the plunger section each include a closing means for releasably closing the tampon compartment and plunger compartment respectively.

8. The storage unit according to claim 7, wherein the closing means is selected from the group consisting of a cap and a seal.

9. The storage unit according to claim 7, wherein the tampon end of the plunger section has an integral closure.

10. The storage unit according to claim 7, wherein the plunger section is adapted to separate from the tampon section after ejection of the tampon.

11. The storage unit according to claim 7, wherein the withdrawal string is a loop.

12. The storage unit according to claim 7, wherein the plunger section includes first and second plunger compartments, the plunger compartments being coaxial to one another.

13. The storage unit according to claim 7, wherein the other menstrual product is selected from the group consisting of panty liners, sanitary napkins, moistened towelettes, and disposal bags.

14. The storage unit according to claim 7, wherein the other menstrual product is a panty liner.

15. The storage unit according to claim 7, wherein the other menstrual product is a moistened towelette.

16. The storage unit according to claim 7, wherein the other menstrual product is a pharmaceutical composition for the relief of menstrual symptoms.

17. The storage unit according to claim 7, wherein the other menstrual product is a disposal bag, the disposal bag being adapted to contain at least one menstrual product for disposal.

18. The storage unit according to claim 17, wherein the disposal bag is a mitt, and the mitt is adapted to cover a hand during cleansing.

19. The storage unit of claim 18, wherein the mitt includes a first layer and a second layer, the first layer being composed of flexible plastic, the second layer being composed of moist towelette material.

20. A feminine hygiene storage unit, comprising:

(a) a tampon section, the tampon section being rigid and generally cylindrical, the tampon section having an outer diameter, a plunger end, an expulsion end, and a tampon compartment, the tampon compartment being adapted to contain a tampon; and (b) a plunger section separate from and attached to the tampon section, the plunger section being coaxial with the tampon section, the plunger section being rigid and generally cylindrical, the plunger section having an outer diameter, a tampon end, a distal end, and at least one plunger compartment, the outer diameter of the plunger section being smaller than the diameter of the tampon compartment, the tampon end of the plunger section being closed, the expulsion end of the tampon section and at least one end of the plunger section each including a closing means for releasably closing the tampon compartment and plunger compartment respectively, the plunger compartment being water resistant and adapted to contain a menstrual product, the tampon end of the plunger section being located within the plunger end of the tampon section, the plunger section being adapted to slide into the tampon compartment.

* * * * *